United States Patent [19]

Kamohara et al.

[11] Patent Number: 5,637,628
[45] Date of Patent: Jun. 10, 1997

[54] SILICONE COMPOSITION FOR DENTAL IMPRESSIONS

[75] Inventors: Hiroshi Kamohara, Matsudo; Shunichi Futami, Nagareyama, both of Japan

[73] Assignee: GC Corporation, Tokyo, Japan

[21] Appl. No.: 505,385

[22] Filed: Jul. 21, 1995

[30] Foreign Application Priority Data

Jul. 29, 1994 [JP] Japan ................................. 6-196248
Jul. 12, 1995 [JP] Japan ................................. 7-197927

[51] Int. Cl.$^6$ ........................................... A61K 6/10
[52] U.S. Cl. .................... 523/109; 524/506; 524/413; 524/448
[58] Field of Search .................... 523/109; 524/506, 524/413, 448

[56] References Cited

U.S. PATENT DOCUMENTS

| | | | |
|---|---|---|---|
| 3,082,527 | 3/1963 | Nitzsche et al. | 523/109 |
| 3,950,300 | 4/1976 | Hittmair et al. | 523/109 |
| 4,096,159 | 6/1978 | Hechtl et al. | 523/109 |
| 4,222,938 | 9/1980 | August et al. | 523/109 |
| 4,273,902 | 6/1981 | Tomioka et al. | 525/479 |
| 4,568,707 | 2/1986 | Voigt et al. | 523/109 |
| 4,965,296 | 10/1990 | Schwabe et al. | 523/109 |

*Primary Examiner*—Ralph H. Dean
*Attorney, Agent, or Firm*—Oblon, Spivak, McClelland, Maier & Neustadt, P.C.

[57] ABSTRACT

A dental impression-taking silicone composition is provided, which comprises A) 100 parts by weight of an organopolysiloxane having at least two aliphatic unsaturated groups per molecule, B) 0.1 to 30 parts by weight of an organohydrogenpoly-siloxane having per molecule at least three hydrogen atoms directly bonded to a silicone atom, C) 10 to 500 ppm of a silicone-soluble platinum compound, as calculated on the basis of the total amount of A) and B), D) 5 to 500 parts by weight of an inorganic filler, and E) 1 to 200 parts by weight of a polyvinyl ether having a polymerization degree of 1,000 to 50,000. This composition provides a paste mixture having an increased strain in compression after curing and a reduced permanent deformation after curing and unlikely to run down during impression-taking. Upon cured, oil matter does not bleed out of the surface of the cured mixture.

8 Claims, No Drawings

SILICONE COMPOSITION FOR DENTAL IMPRESSIONS

BACKGROUND OF THE INVENTION

The present invention relates generally to a dental impression material used for preparing a model of teeth or mouths that are required for making dental prostheses such as crowns, inlays and dentures, and more particularly to a silicone composition for dental impressions that is used as precise impression materials.

Among dental elastic impression materials so far used in the prior art, there are agar, alginate, polysulfide rubber, polyether and silicone rubber-based materials.

An elastic impression material, because it is deformed upon removal from within the mouth but is immediately restored to its original form, can be used to obtain negative copies of teeth, rows of teeth, jaws and oral mucosa, all having complicated shape with undercuts.

Agar and alginate impression materials are of clinically suitable elasticity but have certain problems. Since they are susceptible to some considerable permanent deformation and contain a large amount of moisture, the obtained impressions are likely to undergo a large dimensional change with time, and are so small in tear strength that they are likely to tear up. They are thus mainly used for the purpose of taking general impressions.

Synthetic rubber impression materials made of polysulfide rubber, polyether rubber and silicone rubber are excellent in the ability to reproduce details, very limited in terms of a dimensional change with time and unlikely to tear up, and so are used for taking precise impressions.

Among these synthetic rubber impression materials, however, the polysulfide rubber gives out some offensive odor and cures at too slow a rate. The polyether rubber is of low elasticity and has some hardness, and is likely to swell in the presence of water as well. The silicone rubber, on the other hand, is most frequently used as a precise impression material because it has a sharp curing property, is excellent in elasticity, and shows an extremely limited dimensional change with time. Depending on how it cures, the silicone rubber is broken down into two types, polycondensation and addition polymerization types. Such room-temperature vulcanizing silicone rubber is now used as a dental silicone impression material. In general, the polycondensation type silicone impression material is provided to a dental technician or dentist in the form of a product which is based on a hydroxydimethylpolysiloxane having hydroxyl groups at both termini and additionally contains an alkyl orthosilicate as a cross-linking agent and an organic tin compound as a catalyst. In use, the dentist then mixes and kneads the base ingredient with the catalyst for curing. On the other hand, the addition polymerization type silicone impression material is cured by the addition polymerization of an organopolysiloxane having an aliphatic unsaturated group and hydrogenpolysiloxane in the presence of a platinum catalyst. The product form provided is usually a two-component paste containing base and catalyst components, as mentioned above. For the reasons of its excellent dimensional precision and curing property, the addition polymerization type silicone impression material is the most frequently used one in the synthetic rubber impression materials.

As mentioned just above, the addition polymerization type silicone impression material has various excellent properties, but it is smaller in elastic strain than the already mentioned alginate impression material mentioned earlier. For this reason, there is a great deal of resistance when the obtained impression is removed from within the mouth and this gives pain to a patient. Especially when the patient has teeth which are shaky, such teeth often come out.

In several attempts, the strain in compression of the addition polymerization type silicone impression material is increased by reducing the amounts of the filler and cross-linking agent contained or, in the alternative, mixing therewith an aliphatic hydrocarbon such as liquid paraffin or a non-reactive oil such as dimethylpolysiloxane oil. When the amount of the filler added is decreased, however, there is a risk that the obtained impression material may decrease in tear strength and so may tear up when it is removed from within the mouth. Another possible risk is that the mixture is likely to run down deep into the throat of a patient during impression-taking. The decrease in the amount of the crosslinking agent leads to a drop in the ability of the mixture to cure, resulting in an increased permanent deformation and a lowering of precision with which an impression is taken. The mixing of the filler and crosslinking agent with liquid paraffin or dimethylpoly-siloxane oil makes the plasticity of the mixture so large that there can be an increased permanent deformation with the bleeding of oil matter out of the surface of the cured mixture. Such bleeding of oil matter offers a problem when gypsum slurry is poured into the obtained impression material to make a model of the mouth, because the wettability of gypsum slurry with respect to the impression material becomes extremely worse. This in turn results in the incorporation of air into the model, so making the model a defective one containing much pores.

Thus, none of the prior methods can make a precise negative copy of details of the teeth and mouth.

An object of the present invention is to provide a silicone composition for taking dental impressions free from the problems in association with such prior materials.

SUMMARY OF THE INVENTION

The inventors have made intensive studies of a dental impression silicone composition that is increased in terms of strain in compression, rich in elasticity with a decreased permanent deformation, unlikely to run down and tear up when used to obtain a negative copy of the teeth and mouth, and is free from oil bleeding after curing, and have consequently found that the above object is achieved by the addition of a polyvinyl ether as an ingredient E) to an addition polymerization type silicone impression material comprising ingredients A), B), C) and D).

More specifically, the present invention provides a silicone composition for taking dental impressions, which comprises:

A) 100 parts by weight of an organopolysiloxane having at least two aliphatic unsaturated groups per molecule, B) 0.1 to 30 parts by weight of an organohydrogenpolysiloxane having per molecule at least three hydrogen atoms directly bonded to a silicone atom, C) 10 to 500 ppm of a silicone-soluble platinum compound, as calculated on the basis of the total amount of A) and B), D) 5 to 500 parts by weight of an inorganic filler, and E) 1 to 200 parts by weight of a polyvinyl ether having a polymerization degree of 1,000 to 50,000.

DETAILED EXPLANATION OF THE INVENTION

In the present invention, the ingredient A) is an organopolysiloxane having at least two aliphatic unsaturated groups per molecule. Preferably, this organopolysiloxane is in a linear form with both termini of the molecular chain hindered with vinylsilyl groups. These terminate vinyl groups may be two or more or, alternatively, may be contained in the molecule.

The ingredient B) is an organohydrogenpoly-siloxane that must have per molecule at least three hydrogen atoms directly bonded to a silicon atom, and serves as a cross-linking agent. When this ingredient B) is used in an amount of 0.1 part or less by weight per 100 parts by weight of the ingredient A), not only is the hardness of the obtained cured mixture decreased, but also the curing rate of the composition is slow. In an amount exceeding 30 parts by weight, the cured mixture becomes too brittle.

The ingredient C) is a silicone-soluble platinum compound typically exemplified by known addition reaction catalysts such as chloroplatinic acid, an alcohol-modified chloroplatinic acid, and chloroplatinic acid/olefin complexes, among which a chloroplatinic acid/vinylsiloxane complex is particularly preferred. The amount of the ingredient C) added lies in the range of 10 ppm to 500 ppm based on the total amount of the ingredients A) and B). At 10 ppm or less, the ingredient makes the curing of the composition too slow. This amount has difficulty when a substance inhibiting the catalytic activity of the platinum compound is present even in slight amounts. At 500 ppm or more, the ingredient makes the curing of the composition too rapid, and incurs an economical disadvantage as well. The silicone-soluble platinum compound such as chloroplatinic acid is preferably dissolved in a solvent such as an alcohol, ketone, ether or hydrocarbon solvent or silicone oil for use.

The ingredient D) or inorganic filler is exemplified by quartz, cristobalite, diatomaceous earth, fused quartz, glass fiber, titanium oxide and fused silica. The amount of the inorganic filler added lies in the range of 5 to 500 parts by weight per 100 parts by weight of the ingredient A). At 5 or less parts by weight, the cured mixture becomes brittle. At 500 or more parts by weight, the mixture has an increased viscosity; so it fails to provide a suitable impression material because there is a great deal of resistance when mixed and kneaded together.

The polyvinyl ether used as the ingredient E) is exemplified by polyvinyl ethyl ether, polyvinyl methyl ether, polyvinyl-n-butyl ether and polyvinyl isobutyl ether. Preferably, the polyvinyl ether has a polymerization degree of 1,000 to 50,000. A polyvinyl ether having a polymerization degree less than 1,000 gives a cured product which oil is likely to bleed oil, whereas a polyvinyl ether having a polymerization degree higher than 50,000 makes it difficult to knead the composition. The content of the polyvinyl ether preferably lies in the range of 1 to 200 parts by weight per 100 parts by weight of the ingredient A). At 1 or less part by weight the mixture is likely to run down and decrease strain in compression, whereas at higher than 200 parts by weight the cured mixture becomes tacky on the surface, resulting in a lowering of its releasability. Thus, it is best that the polyvinyl ether is used in an amount of 10 to 150 parts by weight.

Unless the properties of the composition of the present invention are adversely affected, various inorganic or organic coloring materials may be used. For instance, mention is made of coloring materials used with ordinary silicone compositions such as Indian red, titanium white, titanium yellow, and cobalt blue.

EXAMPLES

To give a detailed account of the present invention, some examples will be given below by way of example but not by way of limitation.

Example 1

Base and catalyst pastes of the following compositions were prepared.

| Base Paste | |
|---|---|
| Dimethylpolysiloxane having a viscosity of 3,000 cps and hindered at both termini of its molecular chain with dimethylvinyl-silyl groups | 100 parts by weight |
| Linear methylhydrogenpolysiloxane containing 40 mol % of methyl-hydrogenpolysiloxane units | 3 parts by weight |
| Quartz | 15 parts by weight |
| Polyvinyl isobutyl ether having a polymerization degree of 5,000 | 150 parts by weight |
| Catalyst Paste | |
| Dimethylpolysiloxane having a viscosity of 3,000 cps and hindered at both termini of its molecular chain with dimethylvinyl-silyl groups | 100 parts by weight |
| Silicone oil solution containing 0.4% by weight of 1,3-divinyltetramethyldisiloxane-platinum complex | 3 parts by weight |
| Quartz | 15 parts by weight |

Equal amounts of the base and catalyst pastes were mixed together by means of a spatula for 30 seconds to measure the strain in compression and permanent deformation of the mixture according to JIS T 6513. It is here to be noted that a greater strain in compression gives a softer cured mixture, while a smaller permanent deformation gives a sharper curing and a smaller deformation.

To make estimation of the running down of the mixture and the tearing of an impression, a negative copy of the teeth and mouth was actually taken. The negative copy or impression was allowed to stand at room temperature for one week to observe what surface the impression showed in. The results are shown in TABLE 1.

Although the strain in compression was some large, the mixture did not run down and the impression did not tear up with no bleeding of oil out of the surface of the cured mixture, as can be understood from TABLE 1. The mixture cured sharply and had a decreased permanent deformation value.

Example 2

Base and catalyst pastes of the following compositions were prepared.

| Base Paste | |
|---|---|
| Dimethylpolysiloxane having a viscosity of 2,500 cps and hindered at both termini of its molecular chain with dimethylvinyl-silyl groups | 100 parts by weight |
| Linear methylhydrogenpolysiloxane containing 40 mol % of methyl-hydrogenpolysiloxane units | 3 parts by weight |
| Quartz | 10 parts by weight |
| Polyvinyl isobutyl ether having a polymerization degree of 20,000 | 20 parts by weight |
| Catalyst Paste | |
| Dimethylpolysiloxane having a viscosity of 2,500 cps and hindered at both termini of its molecular chain with dimethylvinyl-silyl groups | 100 parts by weight |

-continued

| | |
|---|---|
| Silicone oil solution containing 0.4% by weight of 1,3-divinyltetramethyldisiloxane-platinum complex | 3 parts by weight |
| Cristobalite | 10 parts by weight |

Equal amounts of the base and catalyst pastes were mixed together by means of a spatula for 30 seconds to measure the strain in compression and permanent deformation of the mixture according to JIS T 6513.

The running down of the mixture and the tearing and surface state of the impression were estimated as in Example 1.

Although the strain in compression was large, the mixture did not run down and the impression did not tear up with no bleeding of oil out of the surface of the cured mixture, as can be understood from TABLE 1. The mixture cured sharply and had a decreased permanent deformation value.

Example 3

Base and catalyst pastes of the following compositions were prepared.

| Base Paste | |
|---|---|
| Dimethylpolysiloxane having a viscosity of 3,000 cps and hindered at both termini of its molecular chain with dimethylvinyl-silyl groups | 100 parts by weight |
| Linear methylhydrogenpolysiloxane containing 40 mol % of methyl-hydrogenpolysiloxane units | 3 parts by weight |
| Quartz | 20 parts by weight |
| Polyvinyl ethyl ether having a polymerization degree of 2,000 | 80 parts by weight |
| Catalyst Paste | |
| Dimethylpolysiloxane having a viscosity of 3,000 cps and hindered at both termini of its molecular chain with dimethylvinyl-silyl groups | 100 parts by weight |
| Silicone oil solution containing 0.4% by weight of 1,3-divinyltetramethyldisiloxane-platinum complex | 3 parts by weight |
| Titanium dioxide | 20 parts by weight |

Equal amounts of the base and catalyst pastes were mixed together by means of a spatula for 30 seconds to measure the strain in compression and permanent deformation of the mixture according to JIS T 6513.

The running down of the mixture and the tearing and surface state of the impression were estimated as in Example 1.

Although the strain in compression was large, the mixture did not run down and the impression did not tear up with no bleeding of oil out of the surface of the cured mixture, as can be understood from TABLE 1. The mixture cured sharply and had a reduced permanent deformation value.

Example 4

Base and catalyst pastes of the following compositions were prepared.

| Base Paste | |
|---|---|
| Dimethylpolysiloxane having a viscosity of 2,500 cps and hindered at both termini of its molecular chain with dimethylvinyl-silyl groups | 100 parts by weight |
| Linear methylhydrogenpolysiloxane containing 30 mol % of methyl-hydrogenpolysiloxane | 35 parts by weight |
| Quartz | 100 parts by weight |
| Polyvinyl methyl ether having a polymerization degree of 5,000 | 200 parts by weight |
| Catalyst Paste | |
| Dimethylpolysiloxane having a viscosity of 2,500 cps and hindered at both termini of its molecular chain with dimethylvinyl-silyl groups | 100 parts by weight |
| Silicone oil solution containing 0.4% by weight of 1,3-divinyltetramethyldisiloxane-platinum complex | 10 parts by weight |
| Quartz | 100 parts by weight |

Equal amounts of the base and catalyst pastes were mixed together by means of spatula for 30 seconds to measure the strain in compression and permanent deformation of the mixture according to JIS T 6513.

The running down of the mixture and the tearing and surface state of the impression were estimated as in Example 1.

Although the strain in compression was large, the mixture did not run down and the impression did not tear up with no bleeding of oil out of the surface of the cured mixture, as can be understood from TABLE 1. The mixture cured sharply and had a decreased permanent deformation value.

Example 5

Base and catalyst pastes of the following compositions were prepared.

| Base Paste | |
|---|---|
| Dimethylpolysiloxane having a viscosity of 2,500 cps and hindered at both termini of its molecular chain with dimethylvinyl-silyl groups | 100 parts by weight |
| Linear methylhydrogenpolysiloxane containing 60 mol % of methyl-hydrogenpolysiloxane unit | 20 parts by weight |
| Fused quartz | 250 parts by weight |
| Polyvinyl methyl ether having a polymerization degree of 5,000 | 300 parts by weight |
| Catalyst Paste | |
| Dimethylpolysiloxane having a viscosity of 2,500 cps and hindered at both termini of its molecular chain with dimethylvinyl-silyl groups | 100 parts by weight |
| Octyl alcohol solution containing 0.5% by weight of alcohol-platinum complex | 1 parts by weight |
| Fused quartz | 250 parts by weight |

Equal amounts of the base and catalyst pastes were mixed together by means of spatula for 30 seconds to measure the strain in compression and permanent deformation of the mixture according to JIS T 6513.

The running down of the mixture and the tearing and surface state of the impression were estimated as in Example 1.

Although the strain in compression was large, the mixture did not run down and the impression did not tear up with no bleeding of oil out of the surface of the cured mixture, as can be understood from TABLE 1. The mixture cured sharply and had a decreased permanent deformation value.

Comparative Example 1

Base and catalyst pastes of the following compositions were prepared.

| Base Paste | |
|---|---|
| Dimethylpolysiloxane having a viscosity of 2,500 cps and hindered at both termini of its molecular chain with dimethylvinyl-silyl groups | 100 parts by weight |
| Linear methylhydrogenpolysiloxane containing 40 mol % of methyl-hydrogenpolysiloxane units | 1 parts by weight |
| Quartz | 10 parts by weight |
| Liquid paraffin | 10 parts by weight |
| Catalyst Paste | |
| Dimethylpolysiloxane having a viscosity of 2,500 cps and hindered at both termini of its molecular chain with dimethylvinyl-silyl groups | 100 parts by weight |
| Silicone oil solution containing 0.4% by weight of 1,3-divinyltetramethyldisiloxane-platinum complex | 3 parts by weight |
| Quartz | 10 parts by weight |

Equal amounts of the base and catalyst pastes were mixed together by means of a spatula for 30 seconds to measure the strain in compression and permanent deformation of the mixture according to JIS T 6513.

The running down of the mixture and the tearing and surface state of the impression were estimated as in Example 1.

As can be seen from the results shown in TABLE 1, the mixture showed an strain in compression smaller than that of each example, had an increased permanent deformation value upon cured due to its slow curing rate, and ran down noticeably. Upon removal from within the mouth, the impression torn at the post portion, and after allowed to stand for one week, oil was found to bleed out of the surface of the impression.

of Comparative Example 1. Nonetheless, the kneaded product in the invention did not run down and no oil bled out of the surfaces of the impressions. The permanent deformation values of Examples 1–5 are up to half that of Comparative Example 1, showing that impressions can be taken with high precision but without tearing.

As can be seen from the foregoing, the dental impression-taking silicone composition containing polyvinyl ether according to the present invention provides a paste mixture having an strain in compression much greater than that of a paste mixture comprising a conventional dental impression material after curing; it is unlikely to run down deep into the throat of a patient, so that it can give no pain to the patient when a negative copy of the teeth and mouth is being made. Nor do shaky teeth come out. Thus, an impression-taking operation can be done with a great safety. The paste mixture, because of having a decreased permanent deformation after curing, enables a precise impression to be taken with no tearing of the post portion, etc. Furthermore, due to no bleeding of oil matter from the surface of the cured mixture and, hence, no lowering of the wettability of gypsum slurry with respect to the impression material, a model of the teeth and mouth can be made with high precision.

Thus, the present invention successfully achieves a dental impression-taking silicone composition having a combination of many features that would not be possible with conventional compositions.

What is claimed is:

1. A dental impression-taking silicone composition, which comprises:
   A) 100 parts by weight of an organopolysiloxane having at least two aliphatic unsaturated groups per molecule,
   B) 0.1 to 30 parts by weight of an organohydrogenpolysiloxane having per molecule at least three hydrogen atoms directly bonded to a silicone atom,
   C) 10 to 500 ppm of a silicone-soluble platinum compound, as calculated on the basis of the total amount of A) and B),
   D) 5 to 500 parts by weight of an inorganic filler, and
   E) 1 to 200 parts by weight of a polyvinyl ether having a polymerization degree of 1,000 to 50,000.

TABLE 1

| | Strain in Compression (%) | Permanent deformation (%) | Running down | Tearing | Surface of impression (after one week) |
|---|---|---|---|---|---|
| Example 1 | 15.0 | 0.3 | not found | not found | no change |
| Example 2 | 11.5 | 0.3 | not found | not found | no change |
| Example 3 | 10.2 | 0.3 | not found | not found | no change |
| Example 4 | 9.3 | 0.5 | not found | not found | no change |
| Example 5 | 8.1 | 0.7 | not found | not found | no change |
| Comparative Example 1 | 7.2 | 1.4 | The mixture ran down noticeably | The impression torn at the post portion | Oil bled out of the surface of the impression |

In Comparative Example 1, the amount of the filler was almost identical with that described in Ex. 2 to make the cured mixture soft and liquid paraffin was used. As shown in TABLE 1, the strain in compression values of Examples 1–5 are within the range of 8.1 to 15.0% that are larger than that 2. The silicone composition according to claim 1, wherein the organopolysiloxane is in a linear form hindered at both termini of its molecular chain with vinylsilyl groups.

3. The silicone composition according to claim 1, wherein the silicone-soluble platinum compound is selected from the group consisting of chloroplatinic acid, an alcohol-modified chloroplatinic acid, and chloroplatinic acid/olefin complexes.

4. The silicone composition according to claim 3, wherein the silicone-soluble platinum compound is used in a solution form with an alcohol, ketone, ether or hydrocarbon solvent, or silicone oil.

5. The silicone composition according to claim 3, wherein the silicone-soluble platinum compound is a chloroplatinic acid/vinylsiloxane complex.

6. The silicone composition according to claim 1, wherein the inorganic filler is selected from the group consisting of quartz, cristobalite, diatomaceous earth, fused quartz, glass fiber, titanium dioxide, and fused silica.

7. The silicone composition according to claim 1, wherein the polyvinyl ether is selected from the group consisting of polyvinyl ethyl ether, polyvinyl methyl ether, polyvinyl-n-butyl ether, and polyvinyl isobutyl ether.

8. The silicone composition according to claim 1, wherein the polyvinyl ether is used in an amount of 10 to 150 parts by weight.

* * * * *